United States Patent [19]

Medina et al.

[11] Patent Number: 4,618,691
[45] Date of Patent: Oct. 21, 1986

[54] CYCLOTRIPHOSPHAZATRIENE-DERIVATIVES

[75] Inventors: Ramiro Medina, Sheffield; Jack M. Sullivan, Florence, both of Ala.

[73] Assignee: Tennessee Valley Authority, Muscle Shoals, Ala.

[21] Appl. No.: 688,101

[22] Filed: Dec. 31, 1984

Related U.S. Application Data

[63] Continuation of Ser. No. 625,424, Jun. 28, 1984, now Defensive Publication No. T105,605.

[51] Int. Cl.$^4$ ............................. C07F 9/22; C12P 3/00
[52] U.S. Cl. ....................................... 558/80; 435/227
[58] Field of Search ...................... 260/927 N; 558/80

[56] References Cited

U.S. PATENT DOCUMENTS 3,206,494 9/1985 Lund et al. ...................... 260/927 N
4,242,325 12/1980 Bayless et al. ...................... 514/138

OTHER PUBLICATIONS

McBee et al., "Chem. Abstracts", vol. 64, (1966), 11242h.
Albright et al., "Chem. Abstracts", vol. 60, (1964), 7955b.

Primary Examiner—Anton H. Sutto
Attorney, Agent, or Firm—Robert A. Petrusek

[57] ABSTRACT

Tests show that 2,2,4,4,6,6-hexaaminocyclotriphosphazatriene, 2-phenoxy-2,4,4,6,6-pentaaminocyclotriphosphazatriene, 2,4-diphenoxy-2,4,6,6-tetraaminocyclotriphosphazatriene and 2,4,6-triphenoxy-2,4,6-triaminocyclotriphosphazatriene (also frequently called phosphonitrilic derivatives) of the formula

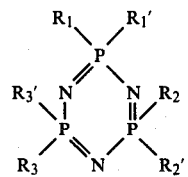

are highly effective inhibitors of urease activity in agricultural soil systems wherein (1) $R_1 \ldots R_3' = NH_2$ or
(2) $R_1' = R_2' = R_3' = R_2 = R_3 = NH_2$ and $R_1 = OC_6H_5$ or
(3) $R_1' = R_2' = R_3' = R_3 = NH_2$ and $R_1 = R_2 = OC_6H_5$ or
(4) $R_1' = R_2' = R_3' = NH_2$ and $R_1 = R_2 = R_3 = OC_6H_5$.

4 Claims, 4 Drawing Figures

CYCLOTRIPHOSPHAZATRIENE-DERIVATIVES

The invention herein described may be manufactured and used by or for the Government for governmental purposes without the payment to us of any royalty therefor.

This is a continuation of application Ser. No. 625,424, filed June 28, 1984, now Def. Pub. No. T105,605 for CYCLOTRIPHOSPHAZATRIENE-DERIVATIVES AS SOIL UREASE ACTIVITY INHIBITORS, Ramiro Medina and Jack M. Sullivan.

INTRODUCTION

The enzyme urease (urea amidohydrolase, EC 3.5.1.5) is a ubiquitous component of many soil systems and has been isolated from a number of microbes and many different plants. In soil systems, urease activities serve to catalyze the hydrolysis of urea to produce ammonia and carbon dioxide according to the reaction:

$$NH_2CONH_2 + H_2O \xrightarrow{urease} 2NH_3 + CO_2$$

The ammonia produced is subsequently hydrolyzed to nutrient ammonium salts.

$$NH_3 + H_2O \rightleftharpoons NH_4^+ + OH^-$$

The $NH_4^+$ is then transformed to $NO_3^-$ by aerobic nitrifying bacteria in the soil.

$$NH_4^+ + 2O_2 \rightarrow NO_3^- + H_2O + 2H^+$$

This sequence of reactions serves a vital function in providing inorganic nitrogen for growing plants. However, urease-induced hydrolysis of urea can cause a considerable loss of volatile ammonia, especially when urea fertilizers are surface applied to agricultural soils [Darrell W. Nelson, Nitrogen in Agricultural Soils, Am. Soc. Agron., Madison, Wis., pp. 327-358 (1982)]. Most of ammonia volatilization from urea occurs in the first week after application. Moderate delays in urea hydrolysis during this time period can greatly reduce ammonia volatilization losses for several reasons. For instance, the farmer has more time to incorporate urea beneath the soil surface before such ammonia losses occur. There is a greater probability of receiving rain with resulting incipient percolation of fertilizer nitrogen values into the soil before such ammonia losses occur. Also, a larger fraction of the applied nitrogen is converted to $NO_3^-$ before being lost as ammonia.

Urea and urea-containing fertilizers presently account for about 30 percent of the fertilizer nitrogen applied in the United States [J. Darwin Bridges, Fertilizer Trends 1982, TVA (1983)], and urea accounts for as much as 60 percent of the fertilizer nitrogen applied worldwide (unpublished TVA data). The trend-line prediction for these percentages is for an increase because urea has a high nitrogen content, low transportation cost, and low production cost relative to alternative nitrogen sources, such as ammonium nitrate and ammonium sulfate. Inasmuch as the relative importance of urea as a primary nitrogen fertilizer is expected to increase to even greater proportions than it now enjoys and substantial amounts of such urea and/or urea-containing fertilizers are applied in situations, such as reduced tillage, pastures, and nonmechanized agriculture, where it is impractical to mechanically incorporate urea to prevent ammonia volatilization, the development of suitable urease inhibitors is an endeavor of considerable importance for both domestic and international agricultural considerations.

Considerable effort is being devoted by a number of research groups in both the private and the public sector to develop suitable urease inhibitors. A particularly promising class of urease inhibitors is compounds containing phosphoroamide groups, $R_xPO(NH_2)_{3-x}$, where $R = NH_2$, OH, phenol, etc. Several researchers in the art have demonstrated that phenyl phosphorodiamidate, $(C_6H_5O)PO(NH_2)_2$, is an extremely potent inhibitor of urease activity [P. Held, S. Lang, E. Tradler, M. Klepel, D. Drohne, H. J. Hartbrich, G. Rothe, H. Scheler, S. Grundmeier, and A. Trautmann, East German Pat. No. 122,177 (Cl. C05G3/08, Sept. 20, 1976), Chem. Abstr. 87:67315W; D. A. Martins and J. M. Bremner, Soil Sci. Soc. Am. J. 48:302-305 (1984)]. Recently Bayless and Millner [U.S. Pat. No. 4,242,325 (1980) and U.S. Pat. No. 4,182,881 (1980)] showed that phosphoryltriamide, $PO(NH_2)_3$ and a series of N-[diaminophosphinyl] arylcarboxamides are also powerful urease inhibitors. Other investigators have shown that diamidophosphoric acid, $PO(NH_2)_2OH$, and monoamidophosphoric acid, $PO(NH_2)(OH)_2$, are also effective urease inhibitors [A. Barth, W. Rollka, and H. J. Michel, Wissenschaftliche Beitraege-Martin Luther Universitaet Halle Wittenberg, No. 2, 5-10 (1980); N. E. Dixon, C. Gazzola, J. J. Waters, R. L. Blakeley, and B. Zerner, J. Am. Chem. Soc. 97:4131 (1975)].

The present invention relates to the discovery that certain materials may be effectively utilized as potent urease activity inhibitors in agricultural soil systems including cyclotriphosphazatriene-derivatives of the formula

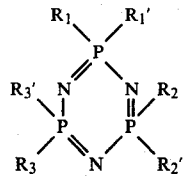

wherein
(1) $R_1 \ldots R_3' = NH_2$ or
(2) $R_1' = R_2' = R_3' = R_2 = R_3 = NH_2$ and $R_1 = OC_6H_5$ or
(3) $R_1' = R_2' = R_3' = R_3 = NH_2$ and $R_1 = R_2 = OC_6H_5$ or
(4) $R_1' = R_2' = R_3' = NH_2$ and $R_1 = R_2 = R_3 = OC_6H_5$

SUMMARY OF THE INVENTION

In arriving at the gist underlying the concept of the instant invention, it was conceived that cyclotriphosphazatriene-derivatives, even though they are not members of the phosphoroamide class of compounds discussed above, should also be investigated as urease activity inhibitors. Although many research groups, especially R. A. Shaw et al. [R. A. Shaw, Phosphorus and Sulfur 4:101-121 (1978)], have concerned themselves with the preparation of cyclotriphosphazatriene-derivatives, the three phenoxyaminocyclotriphosphazatrienes presented above are thought to be actually new compounds, reported now for the first time, because no information about their preparation and chemistry has been found. Of the compounds of interest, only the 2,2,4,4,6,6-hexaaminocyclotriphosphazatriene (phosphonitrilic hexaamide) has been reported. The aqueous solution hydrolysis of 2,2,4,4,6,6-hexaaminocyclotriphosphazatriene was studied by Dostal, Kouril, and Novak [K. Dostal, M. Kouril, and J. Novak (J. E. Purkyne Univ., Brno, Czech.) *Z. Chem.* 4(9):353 (1964), (*Chem. Abstr.* 62: 4670,g)]. They report that the aqueous solution hydrolysis of 2,2,4,4,6,6-hexaaminocyclotriphosphazatriene proceeds by the following sequence of reaction steps:

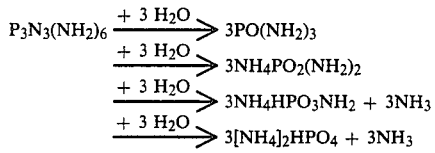

Hence, the hydrolysis of 2,2,4,4,6,6-hexaaminocyclotriphosphazatriene produces phosphoryltriamide and a consecutive series of ammonium salts of phosphoroamide compounds, all of which have been demonstrated supra to be urease activity inhibitors.

In this in vitro experiment (in an enzyme and soil free system) the reaction temperature employed by Dostal, Kouril, and Novak was not reported; however, similar studies conducted in TVA laboratory tests required a minimum temperature of 70° C. in order to obtain conveniently measurable reaction rates (unpublished data, TVA, 1974).

These results are also in agreement with the publication of W. Töpelmann and coworkers [W. Töpelmann, H. Kroschwitz, D. Schröter, D. Patzig, and H. A. Lehmann, *Z. Chem.* 19:273–380 (1979)], where the hydrolysis of 2,2,4,4,6,6-hexaaminocyclotriphosphazatriene was conducted by pH 8 and temperatures of 15° C. and 30° C., hydrolyzing very slowly in about 300 and 100 hours, respectively. They demonstrated also, that not only phosphoryltriamide and phosphoryldiamide were produced during the hydrolysis but also different imidoamidopolyphosphates in significant amounts, which could also have urease inhibitory properties.

An investigation by Dick and Tabatabai [W. A. Dick and M. A. Tabatabai, *Geoderma* 21:175–182 (1978)] showed that hexaaminocyclotriphosphazatriene hydrolyzed very slowly (6–13 percent hydrolyzed in 7 days) in three different soil systems at 20° C.

Although the literature teaches that 2,2,4,4,6,6-hexaaminocyclotriphosphazatriene exhibits characteristics such that it appears to resist hydrolysis both in vitro and in vivo. i.e., in laboratory solutions at or near room temperature and in many soil systems during spring or early summer applications, respectively. We have unexpectedly found that hexaaminocyclotriphosphazatriene and the phenoxyaminocyclotriphosphazatrienes are excellent urease inhibitors.

Some nitrogen-containing heterocyclic compounds such as triazole derivatives or a N-ethylmaleinimide having structures similar to the cyclotriphosphazatrienes have been reported to be effective urease inhibitors in experiments with the isolated enzyme [P. Mildner and B. Mihanovic, *Croat. Chem. Acta* 46:79–82 (1974)] and also in soil experiments, with the herbicide 3-amino-1,2,4-triazole [S. M. Gauthier, S. S. Ashtakala, and J. A. Lenoir, *Hort Science* 11:481–482 (1976)]. It may be possible that the two inhibitor classes have substantially the same mechanism of inhibition, to wit, reacting with the essential sulfhydryl group(s) on the active site(s) of the urease. At this time, however, we can only speculate that the inhibitory properties of the cyclotriphosphazatriene derivatives result either from some yet unidentified chemical properties and/or characteristics of the compounds themselves. If the mechanism is related to reacting with, or inhibiting of such sulfhydryl group(s), it might be classified as irreversible inhibition but more probably as competitive inhibition.

Several hundred scientific papers have been published on urease since Sumner (1926) first produced the classical octahedral crystals and showed that the enzyme was a protein, but it was in 1969 that Zerner's group [R. L. Blakeley, E. C. Webb, and B. Zerner, *Biochemistry* 8:1984–1990 (1969)] prepared a highly purified urease with a full specific activity and in at least 99% a homogeneous state. They established with this preparation a reproducible molecular weight (about 590,000) and proposed that the molecule contained six subunits with asparagine as the N-terminal amino acid. Although Previous work [J. F. Ambrose, G. B. Kistiakowsky, and A. G. Kridl, *J. Amer. Chem. Soc.* 73:1232 (1951)] had indicated that four or eight essential SH-groups were involved in the urea-hydrolysis reaction, Zerner's group could only confirm that the active site SH-groups "react slowly with N-ethylmaleimide," but they were unable to define unequivocally the number of "essential SH groups" in the 590,000 molecular weight species. In addition, Kobashi et al. [K. Kobashi, J. Hase, and T. Komai, *Biochem. Biophys. Res. Commun.* 23:34 (1966)] on the basis of inhibition by hydroxamic acids suggested that the number of active sites in the 590,000 molecular-weight species of sword bean urease was 2. These results seem to be confirmed by the discovery that highly purified urease from jack bean [N. E. Dixon, C. Gazzola, R. L. Blakeley, and B. Zerner, *J. Am. Chem. Soc.* 97:4131 (1975)] and from tobacco, rice, and soybean [J. C. Polacco, *Plant Science Letters* 10:249–255 (1977)] contained stoichiometric amounts of nickel (2 atoms per active site), demonstrating simultaneously the first biological role definitely assigned to nickel. Over the last few years considerable effort has been made to elucidate the mechanism of the urease reaction. Although attempts to demonstrate the formation of a carbamoyl-enzyme intermediate, which was postulated many years ago, have so far failed, Zerner's group [N. E. Dixon, P. W. Riddles, C. Gazzola, R. L. Blakeley, and B. Zerner, *Can. J. Biochem.* 58:1335–1344 (1980)] proposed a mechanism of reaction on the base of a carbamoyl-transfer reaction and where the substrate is activated toward nucleophilic attack by 0-coordination to a $Ni^{2+}$ ion. Both $Ni^{2+}$ ions are involved in this proposed mechanism. A second mechanism of reaction based on the determination of kinetic isotope effects [R. Medina, T. Olleros, and H. L. Schmidt, IN *Proc.* 4th Int. Conference on Stable Isotopes, pp. 77–82, H.L. Schmidt, H. Förstel, K. Heizinger (Eds.), Jülich, March 1981, Elsevier, Amsterdam (1982)] was proposed. These results indicated the existence of an enzyme bound carbamate intermediate and demonstrated that the enzyme-Ni-substrate complex decomposes releasing the first $NH_3$ in a slow, rate-limiting step.

An additional complication develops from the tendency of the urease to form polymers and isozymes changing the properties of the original monomeric enzyme and probably the mechanism of reaction [W. N. Fishbein and K. Nagarajan, *Arch. Biochem. Biophys.*

144:700–714 (1971)]. Finally the properties of soil urease differ significantly from those of ureases from other sources [J. M. Bremner and R. L. Mulvaney, IN *Soil Enzymes*, pp. 149–196, R. G. Burns (Ed.), Academic Press (1978)], and it is much more difficult to obtain reliable kinetic data for enzymes in heterogeneous environments, such as soil, than for enzymes in homogeneous solutions.

While many urease inhibitors have been identified, few kinetic descriptions include the type of inhibition. The reversible and competitive inhibition of sword bean urease by a wide variety of hydroxamic acids was discovered by Kobashi et al. [K. Kobashi, J. Hase, K. Uehara, *Biochim. Biophys. Acta* 65:380–383 (1962)]. Kinetic and spectral studies performed by B. Zerner and coworkers [N. E. Dixon, J. A. Hinds, A. K. Fihelly, C. Gazzola, D. J. Winzor, R. L. Blakeley, and B. Zerner, *Cand. J. Biochem.* 58:1323–1334 (1980)] established that hydroxamic acids were reversibly bound to active-site nickel ions in jack bean urease. Chemical and physical studies of the enzymatically inactive phosphoramidate-urease complex provide convincing evidence that phosphoramidate binds reversibly to the active-site nickel ion [N. E. Dixon, R. L. Blakeley, and B. Zerner, *Can. J. Biochem.* 58:481–488 (1980)].

The kinetics of urease inhibition by phenyl phosphorodiamidate which demonstrates a competitive inhibition and hydroquinone which exemplifies a mixed inhibition mechanism were performed by L. J. Youngdahl and E. R. Austin at IFDC (unpublished results). A kinetic study of the soil urease inhibition by six substituted ureas, compounds which are used as herbicides, showed that all six compounds exhibited mixed inhibition characteristics (competitive and noncompetitive) [S. Cervelli, P. Nannipieri, G. Giovannini, and A. Perna, *Pesticide Biochem. Physiol.* 5:221–225 (1975)].

There are very few additional publications on kinetic studies concerning soil ureases [J. M. Bremner and R. L. Mulvaney, IN *Soil Enzymes*, pp. 149–196. R. G. Burns (Ed.), (1978)]. The main work in this area has been to establish the inhibitory properties of potential test compounds, irrespective of the kind of inhibition that is responsible for the retardation of the urea hydrolysis. However, the successful use of this technology by the fertilizer industry does not require that the mechanism be identified.

Taking into consideration all of this information one can establish that even though urease has been extensively studied for about 60 years, the mechanism of action and the mechanism of inhibition of this enzyme, especially in heterogeneous environments such as soils are, at best, only partially known.

OBJECT OF THE INVENTION

The principal object of the present invention is to identify and characterize a group of highly effective inhibitors which will, when admixed with urea or urea-containing fertilizers, prevent or greatly reduce the loss of ammoniacal nitrogen from agricultural soils resulting from the urease-induced hydrolysis urea.

While cyclotriphosphazatriene-derivatives have now been identified as effective inhibitors for the purpose of the present invention, it is now postulated in view of information gleaned by reducing the present invention to practice that perhaps many derivatives of the above compounds which contain the PN cyclic structure, especially the cyclotetraphosphazatetraene derivatives, are also potentially effective urease inhibitors. For example, the following compounds having the same skeleton structure of cyclic PN but with the R groups replaced with other radicals or elements, such as:

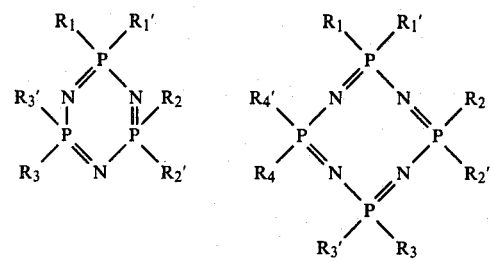

where $R_1$ to $R_4'$ may be hydrogen or the following functional groups: halogen, pseudohalogen, hydroxy, sulfhydryl, alkyl or substituted alkyl, alkenyl or substituted alkenyl, alkynyl or substituted alkynyl, aryl or substituted aryl, amino or substituted amino, hydrazino or substituted hydrazino, acyl or substituted acyl, aroyl or substituted aroyl, alkoxy or substituted alkoxy, aryloxy or substituted aryloxy, thioalkoxy or substituted thioalkoxy, thioaryloxy or substituted thioaryloxy, anilino or substituted anilino, heterocyclic or substituted heterocyclic, as well as combinations of the above, etc., are likely to be effective urease inhibitors. A further opportunity to capitalize on our observations to date may be effected by the use of the parent materials, supra, polymerized to the appropriate degree to yield the optimum combination of solubility and inhibitory effect upon the urease enzyme.

It will now, of course, be appreciated that the substitution suggested supra for the $R_1$ to $R_4'$ groups on the original skeleton structure could lead those skilled in the art to the testing and investigation of great multiplicity of compounds. We have been particularly interested in investigating the characteristics of the following three derivatives, to wit, $P_3N_3[N(CH_3)_2]_6$, 2,2,4,4,6,6-hexa(dimethylamino)cyclotriphosphazatriene; $P_3N_3(NHCH_3)_6$, 2,2,4,4,6,6-hexa(monomethylamino)cyclotriphosphazatriene and $P_3N_3(NH_2)_2N(CH_3)_2]_4$, 2,2,4,4,-tetra(dimethylamino)-6,6-diaminocyclotriphosphazatriene. Test results of these three materials as well as others as set forth in Example III, infra, show that these materials do not exhibit urease inhibition.

Similar soil tests performed with $P_3N_3(Cl)_5(OC_6H_5)$, 2-phenoxy-2,4,4,6,6-pentachlorocyclotriphosphazatriene; $P_3N_3(Cl)_4(OC_6H_5)_2$, 2,4-diphenoxy-2,4,6,6, tetrachlorocyclotriphosphazatriene; and $P_3N_3(Cl)_3(OC_6H_5)_3$, 2,4,6-triphenoxy-2,4,6-trichlorocyclotriphosphazatriene, showed that these compounds also are not effective urease inhibitors.

DESCRIPTION OF THE DRAWINGS

The present invention, together with further objects and advantages thereof, will be better understood from a consideration of the following description taken in connection with the accompanying drawing in which:

FIGS. 2 to 4 are discussed in detail, in Example VI infra.

Referring more specifically to FIG. 1, the results presented therein were plotted and extrapolated on the basis of the data contained at least in part in Table V and using J. M. Bremmer's concept of the percentage urease inhibition* L. A. Douglas and J. M. Bremner, *Soil Biol. Biochem.*, 3:309-315 (1971)]. FIG. 1 shows the different degrees of inhibition of the cyclotriphosphazatrienes compared to PPDA, which has a higher initial percentage of urease inhibition but decreases to 0% in less than 9 days. The 2-phenoxy-2,4,4,6,6 pentaaminocyclotriphosphazatriene and 2,4-diphenoxy-2,4,6,6 tetraaminocyclotriphosphazatriene show a slightly longer period of urease inhibition but also approach 0% inhibition in about 10 days.

Figure 1:
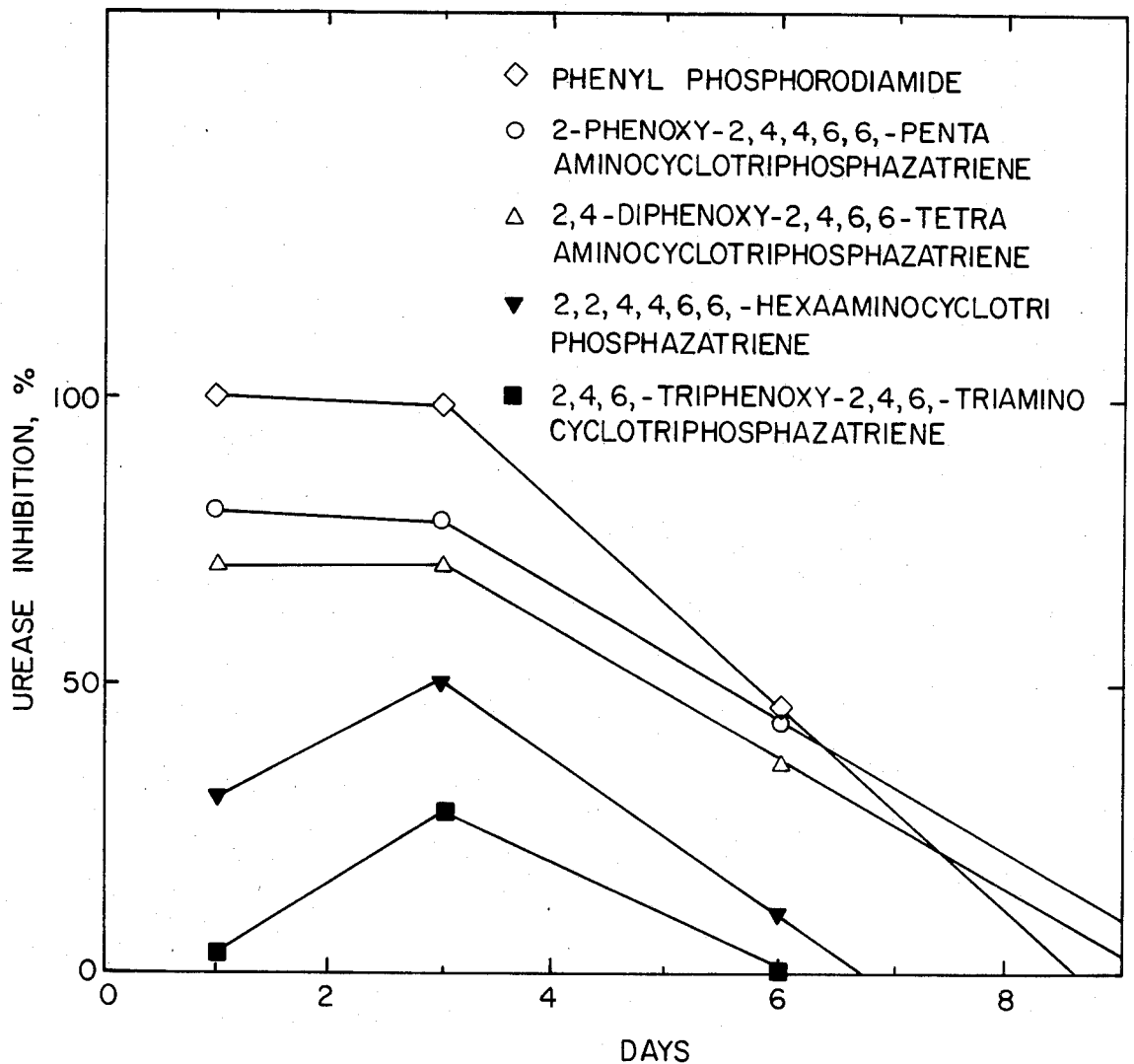
FIG. 1 is a graphical illustration of urease activity inhibition as a function of time.

$$*UI\ [\%] = \frac{A - B}{C - B} \times 100.$$

UI[%]: Urease inhibition in percent.
A: Amount of urea found after incubation of soil sample treated with test compound.
B: Amount of urea found after incubation of soil sample not treated with test compound.
C: Amount of urea added at the beginning of the test (t=o).

DESCRIPTION OF PREFERRED EMBODIMENTS

For ease and convenience of application, the cyclotriphosphazatriene derivatives may be incorporated into urea or urea-containing fertilizers by: mixing, prilling, granulating, coating, or other means familiar to those knowledgeable in the art of producing and/or blending fertilizer materials.

Examples I, II, IV, V, and VI, infra, are in the nature of positive examples and depict the rather significant effect that 2,2,4,4,6,6-hexaaminocyclotriphosphazatriene, 2-phenoxy-2,4,4,6,6-pentaaminocyclotriphosphazatriene, 2,4-diphenoxy-2,4,6,6-tetraaminocyclotriphosphazatriene, and 2,4,6-triphenoxy-2,4,6-triaminocyclotriphosphazatriene exhibit as soil urease activity inhibitors.

Example III, infra, is offered in the manner of a negative example and shows various compounds, including the derivatives mentioned supra, that do not act as or display characteristics having utility as soil urease activity inhibitors.

In order that those skilled in the art can better understand and appreciate the work reported herein, brief descriptions, infra, of the testing methods employed are given before the specifics of Examples I, II, III, IV, V, and VI are discussed.

Testing Methods

Urease activity inhibitor test compounds may be evaluated either in aqueous or in soil systems. When aqueous systems are used, urea plus a test compound with possible urease inhibition activity and relatively pure urease enzyme are incubated together to determine the effects of the test compound on urease-catalyzed hydrolysis of urea. When soil systems are used, urea and the test compound are added to moist soil, and the urease enzyme is supplied from the soil. The main disadvantage of using soil systems is that the true activity of test compounds may be masked because of reactions between the test compound and soil. Thus, basic studies for understanding chemical structure-activity relationships are usually done in aqueous systems. However, soil systems must be used to determine the principal applicability of test compounds since soil can significantly modify inhibitory effects of these compounds.

The most common and conventional method for evaluating potential urease inhibitors in soil systems is to mix both urea and the test compound throughout the soil and determine the effects of the test compound on rate of urea hydrolysis [L. A. Douglass and J. M. Bremner, *Soil Biol. Biochem.* 3:309-315 (1971); J. M. Bremner and R. L. Mulvaney, Urease Activity in Soils, Chapter 5, IN *Soil Enzymes* pp. 149-195, R. G. Burns (Ed.), Academic Press, (1978)].

Test compounds in Example IV, infra, were evaluated using this method as follows: 100 g of a urease active soil (Hastings silt loam), 40 ml $H_2O$, 410 mg of urea powder, and 41 mg of powdered inhibitor were mixed well in a 0.25-liter cylindrical polystyrene container (6×9.8 cm) before incubation. The containers were capped and placed in an incubator maintained at 25°0 C. After 1, 3, and 6 days, the 100 g soil sample was extracted with 250 ml of 2M KCl containing 5 ppm of phenyl phosphorodiamidate. The KCl-PPDA extracts were analyzed on the Auto Analyzer 11 [Technicon method No. 40001 FD4, Technicon, Tarrytown, N.Y., U.S.A. (1974)].

Test compounds in Examples I, II, III, and V, infra, were evaluated in soil systems by an alternative procedure in which powdered mixtures of urea and test compounds were applied in narrow bands in the soil rather than being mixed throughout the soil. The banded configuration is not only applicable to banded applications, but also results in concentration gradients of urea, urea hydrolysis products, test compounds, and test compound decomposition products similar to those in the immediate vicinity of urea granules containing test compounds. Another advantage of the banded configuration compared with mixing throughout the soil is that slightly soluble test compounds can be easily band applied, whereas it is difficult to achieve a known degree of mixing of a small quantity of slightly soluble test compound with soil. The banded configuration also enables testing for urease inhibition under realistic soil conditions prior to the development of techniques for cogranulating a wide range of test compounds with urea.

Specifics of the procedure for evaluating test compounds (Examples I, II, III, and V) were the following. Urease active soil (Hastings silt loam) was moistened to a moisture content of 20 percent (dry weight basis) and preincubated at room temperature for 2 days. Plexiglas containers (6×6×6 cm) were one-half filled with soil and packed to a bulk density of 1.1 $g/cm^3$. Urea or urea plus inhibitor (thoroughly mixed) was distributed in a narrow band, 6 cm long on the soil surface. The containers were then filled with soil, again packing to a bulk density of 1.1 $g/cm^3$. The containers were incubated at 25° C. for the desired reaction period after which the containers were frozen to about −5° C. to stop urea hydrolysis. Immediately prior to extracting the remaining urea from the soil, said soil was allowed to thaw. Soil from each container was thoroughly mixed, and a 10-g sample was extracted with 100 ml of 2M KCl containing phenylmercuric acetate to prevent urea hydrolysis during handling [L. A. Douglass and J. M. Bremner, *Soil Sci. Soc. Am. Proc.* 34:859-862 (1970)].

Urea in the extracts was determined with an automated version of the colorimetric procedure [L. A. Douglass and J. M. Bremner, *Anal. Letters* 3(2):79–87 (1970)].

Test compounds in Example VI, infra, were evaluated in soil systems by a modification of the Douglass and Bremner [L. A. Douglass and J. W. Bremner, *Soil Siol. Biochem.* 3:309–315 (1971)] procedure in which solutions or suspensions of the test compounds were mixed throughout the soil. Then at selected time intervals, urea was added to the soil-inhibitor mixtures. The advantage of this procedure is that soil urease inhibition by the test compounds can be detected for time periods lasting up to several weeks or longer. Rapid urea hydrolysis in other test procedures may limit their applicability to test compounds that have slow and sustained inhibition properties. As was previously demonstrated in FIG. 2 and at least in part by the data in Table VII of Example VI infra, the test compounds show slow and sustained inhibitory properties.

Specifics of the procedure for evaluating the test compounds in Example VI were the following. Urease active soil (Crowley silt loam from Louisiana) was moistened to a moisture content of 16% (dry weight basis) and preincubated at room temperature for 2 days. One milliliter of solution or suspension containing 7 micromoles of each test compound was added to 120 g of moist soil and mixed well. Polyvinylchloride cylinders 12 cm long and 4 cm in diameter were filled with the inhibitor-soil mixture and packed to a bulk density of about 0.9 g/cm$^3$ and covered with a perforated plastic film. These columns of inhibitor-soil mixtures plus untreated check columns were incubated at 30° C. for periods of 0, 3, 7, 14, and 21 days at constant moisture content. At each time interval, 1 ml of urea solution containing 50 mg of urea was mixed well with the inhibitor-soil mixture from a single column. The urea-inhibitor-soil mixture was packed in a column to a bulk density of about 0.9 g/cm$^3$, covered with a perforated plastic film, and reincubated for 16 hours at 30° C. Following the 16 hours of reincubation, about 120 g of the urea-inhibitor-soil mixture was extracted with 250 ml of 2M KCl containing 5 ppm of phenylphosphorodiamidate. The KC1-PPDA extracts were analyzed on the Auto Analyzer II [Technicon method No. 40001 FD4, Technicon, Tarrytown, N.Y., U.S.A. (1974)]. Three replicates were used on all treatments and checks.

EXAMPLES

In order that those skilled in the art may better understand how the present invention can be practiced, the following examples are given by way of illustration and not necessarily by way of limitation. Names of compounds used in the examples and their chemical formulas are shown in Table I below.

TABLE I

| Compounds and Chemical Formulas | |
|---|---|
| Name | Formula |
| Phenyl phosphorodiamidate | $(C_6H_5O)PO(NH_2)_2$ |
| Phosphoryltriamide | $PO(NH_2)_3$ |
| Acetohydroxamic acid | $CH_3C(NOH)(OH)$ |
| Hydroxyurea | $CO(NH_2)(NHOH)$ |
| Ammonium thiocyanate | $NH_4SCN$ |
| Thiourea | $CS(NH_2)_2$ |
| 2,2,4,4,6,6-hexaaminocyclotri-phosphazatriene | $P_2N_3(NH_2)_6$ |
| 2,2,4,4,6,6-hexachlorocyclotri-phosphazatriene | $P_3N_3Cl_6$ |
| 2,2,4,4,-tetra(monomethylamino)-6,6-diaminocyclotriphosphazatriene | $P_3N_3(NH_2)_2(NHCH_3)_4$ |

TABLE I-continued

| Compounds and Chemical Formulas | |
|---|---|
| Name | Formula |
| 2,2,4,4,6,6-hexa(dimethylamino)cyclotriphosphazatriene | $P_3N_3[N(CH_3)_2]_6$ |
| 2,2,4,4,6,6-hexa(monomethylamino)cyclotriphosphazatriene | $P_3N_3(NHCH_3)_6$ |
| 2,2,4,4-tetrachloro-6,6-di(dimethylamino)cyclotriphosphazatriene | $P_3N_3Cl_4[N(CH_3)_2]_2$ |
| 2-phenoxy-2,4,4,6,6-pentaaminocyclotriphosphazatriene | $P_3N_3(NH_2)_5(OC_6H_5)$ |
| 2,4-diphenoxy-2,4,6,6-tetraaminocyclotriphosphazatriene | $P_3N_3(NH_2)_4(OC_6H_5)_2$ |
| 2,4,6-triphenoxy-2,4,6-triaminocyclotriphosphazatriene | $P_3N_3(NH_2)_3(OC_6H_5)_3$ |
| 2-phenoxy-2,4,4,6,6-pentachlorocyclotriphosphazatriene | $P_3N_3Cl_5(OC_6H_5)$ |
| 2,4-diphenoxy-2,4,6,6-tetrachlorocyclotriphosphazatriene | $P_3N_3Cl_4(OC_6H_5)_2$ |
| 2,4,6-triphenoxy-2,4,6-trichlorocyclotriphosphazatriene | $P_3N_3Cl_3(OC_6H_5)_3$ |

EXAMPLE 1

2,2,4,4,6,6-hexaaminocyclotriphosphazatriene was prepared from 2,2,4,4,6,6-hexachlorocyclotriphosphazatriene and anhydrous ammonia by the procedure of Sowerby and Audrieth [D. B. Sowerby and L. F. Audrieth, *Chem. Ber.* 94:2670 (1961)]. Its relative effectiveness, versus a number of other known urease inhibitors, was tested by the following procedure. Urease active soil (Hastings silt loam) was moistened to a moisture content of 20 percent and Preincubated at room temperature for 2 days. Plexiglas containers (6×6×6 cm) were one-half filled with soil and packed to a bulk density of 1.1 g/cm$^3$. Urea or urea plus inhibitor (thoroughly mixed) was distributed in a narrow band, 6 cm long, on the surface of the soil. The containers were then filled with soil and again packed to a bulk density of 1.1 g/cm$^3$. The containers were incubated at 25° C. for the desired reaction period. The soil from each container was thoroughly mixed, and a 10-g sample was extracted with 100 ml of 2M KCl containing 5 ppm phenylmercuric acetate to prevent urea hydrolysis during handling [L. A. Douglas and J. M. Bremner, *Soil Sci. Soc. Am. Proc.* 34:859–862 (1970)]. The urea in the extracts was determined colorimetrically as a measure of the unhydrolyzed urea. The results of 3-day and 6-day tests for equimolar inhibitor contents are given in Table II below. These results show the 2,2,4,4,6,6-hexaaminocyclotriphosphazatriene is comparable to PPDA as an inhibitor of soil urease activity. In 3-day tests, its performance exceeds that of all other inhibitors tested, except phenyl phosphorodiamidate. Its longer term effectiveness (6 days) is even greater than that of phenyl phosphorodiamidate.

TABLE II

Urea Hydrolysis in Bands of Urea as Affected by Various Urease Inhibitors[a] (Equimolar Basis) in Three Replications With Hastings Silt Loam Soil at 25° C.

| N Source | Weight mg/Band | Inhibitor | Weight, mg/Band | Unhydrolyzed Urea, % 3 Days | 6 Days[b] |
|---|---|---|---|---|---|
| Urea | 410[c] | — | | 0.4 | 0.2 |
| Urea | 410 | $(C_6H_5O)PO(NH_2)_2$ | 43[d] | 68.3 | 12.9 |
| Urea | 410 | $(PO(NH_2)_3)$ | 23 | 43.4 | 1.8 |
| Urea | 410 | $CH_3C(NOH)(OH)$ | 19 | 26.2 | 6.7 |
| Urea | 410 | $CO(NH_2)(NHOH)$ | 19 | 20.3 | 0.2 |

TABLE II-continued

Urea Hydrolysis in Bands of Urea as Affected by Various Urease Inhibitors[a] (Equimolar Basis) in Three Replications With Hastings Silt Loam Soil at 25° C.

| N Source | Weight, mg/Band | Inhibitor | Weight, mg/Band | Unhydrolyzed Urea, % 3 Days | 6 Days[b] |
|---|---|---|---|---|---|
| Urea | 410 | NH$_4$SCN | 19 | 3.5 | 0.5 |
| Urea | 410 | CS(NH$_2$)$_2$ | 19 | 16.2 | 0.4 |
| Urea | 410 | P$_3$N$_3$(NH$_2$)$_6$ | 57 | 48.1 | 16.8 |

[a] The soil urease inhibitory properties of a number of the tested compounds have also been demonstrated by other investigators:
Acetohydroxamic acid - [K. B. Pugh and J. S. Waid, Soil. Biol. Biochem. 1:195–206 (1969)].
Hydroxyurea - [W. N. Fishbein, T. S. Winter, and J. D. Davidson, J. Biol. Chem. 240:2402–2406 (1965)].
Ammonium thiocynate - Unpublished TVA data.
Thiourea - [S. S. Malhi and M. Nyborg, Plant and Soil 51:177–186 (1979)].
Phenyl phosphorodiamidate and phosphoryltriamide - [D. A. Martins and J. M. Bremner, Soil Sci. Soc. Am. J. 48:302–305 (1984)].
[b] Urea was completely hydrolyzed in all treatments in 9 days.
[c] N rate equivalent to 100 kg/ha applied in bands 30 cm apart. N source weights are for a band 6 cm long and represent 6.72 moles urea/band.
[d] Inhibitor weights represent 0.25 millimoles inhibitor/band.

EXAMPLE II

The results of tests similar in procedure to those utilized in Example I, supra, in which 2,2,4,4,6,6-hexaaminocyclotriphosphazatriene, phosphoryltriamide, and phenyl phosphorodiamidate were tested at equal weight contents (10 percent) are shown in Table III below. Again the performance of 2,2,4,4,6,6-hexaaminocyclotriphosphazatriene exceeds that of phosphoryltriamide in 3-day tests and is much more effective in 6-day tests.

TABLE III

Urea Hydrolysis in Bands of Urea as Affected by Urease Inhibitors Applied at a Rate of 10 Percent of Urea (wt/wt Basis); Four Replications With Hastings Silt Loam Soil at 25° C.

| N Source | Weight, mg/Band | Inhibitor | Weight, mg/Band | Unhydrolyzed Urea, % 3 Days | 6 Days |
|---|---|---|---|---|---|
| Urea | 410[a] | (C$_6$H$_5$O) | 41 | 69.0 | 1.8 |
| Urea | 410 | OP(NH$_2$)$_3$ | 41 | 48.1 | 1.1 |
| Urea | 410 | P$_3$N$_3$(NH$_2$)$_6$ | 41 | 49.7 | 9.5 |
| Urea | 410 | — | — | 0.0 | 0.0 | a. N rate equivalent to 100 kg/ha applied in bands 30 cm apart; N source weights are for a band 6 cm long.

EXAMPLE III

The tests comprising this example were conducted along the same lines and with similar procedures as outlined in Example I, supra. The results of these tests, which are tabulated in Table IV below, show that a number of derivatives of 2,2,4,4,6,6-hexaaminocyclotriphosphazatriene, wherein some or all of the hydrogens were substituted for by various groups, such as halogen and methyl, did not live up to expectations in that they did not prove to be effective urease inhibitors.

TABLE IV

Urea Hydrolysis in Bands of Urea as Affected by Urease Inhibitor Test Compounds Applied at a Rate of 10 Percent of Urea (wt/wt Basis); Two Replications With Hastings Silt Loam Soil

| N Source | Weight, mg/Band | Inhibitor | Weight, mg/Band | Unhydrolyzed Urea, % 3 Days | 6 Days |
|---|---|---|---|---|---|
| Urea | 410[a] | (C$_6$H$_5$O)PO(NH$_2$)$_2$ | 41 | 62.6 | 10.1 |
| Urea | 410 | PO(NH$_2$)$_3$ | 41 | 54.2 | 2.6 |
| Urea | 410 | P$_3$N$_3$(NH$_2$)$_6$ | 41 | 53.8 | 9.5 |
| Urea | 410 | P$_3$N$_3$Cl$_6$ | 41 | 3.2 | 0.0 |
| Urea | 410 | P$_3$N$_3$(NH$_2$)$_2$(NHCH$_3$)$_4$ | 41 | 0.5 | 0.0 |
| Urea | 410 | P$_3$N$_3$[N(CH$_3$)$_2$]$_6$ | 41 | 0.0 | 0.0 |
| Urea | 410 | P$_3$N$_3$(NH$_2$)$_6$ + HCHO | 41 | 3.1 | 0.0 |
| Urea | 410 | P$_3$N$_3$(NHCH$_3$)$_6$ | 41 | 0.0 | 0.0 |
| Urea | 410 | P$_3$N$_3$Cl$_4$[N(CH$_3$)$_2$]$_2$ | 41 | 0.0 | 0.0 |
| Urea | 410 | — | — | 0.9 | 0.0 | a. N rate equivalent to 100 kg/ha applied in bands 30 cm apart; N source weights are for a band 6 cm long.

EXAMPLE IV 2-phenoxy-2,4,4,6,6-pentachlorocyclotriphosphazatriene, 2,4-diphenoxy-2,4,6,6-tetrachlorocyclotriphosphazatriene, and 2,4,6-triphenoxy-2,4,6-trichlorocyclotriphosphazatriene were prepared from sodium phenoxide and 2,2,4,4,6,6-hexachlorocyclotriphosphazatriene by the procedure of Dell, Fitzsimmons, and Shaw [D. Dell, B. W. Fitzsimmons, and R. A. Shaw, J. Chem. Soc., 4070 (965)]. These compounds were aminated with anhydrous ammonia in a Parr bomb to yield pure 2-phenoxy-2,4,4,6,6-pentaaminocyclotriphosphazatriene, 2,4-diphenoxy-2,4,6,6-tetraaminocyclotriphosphazatriene, and 2,4,6-triphenoxy-2,4,6-triaminocyclotriphosphazatriene. The relative inhibition of the amino compounds versus the known soil urease inhibitor, phenyl phosphorodiamidate, was tested by the following procedure. Following the procedure of Douglas and Bremner, [L. A. Douglas and J. M. Bremner, Soil Sci. Soc. Am. Proc. 34:859–862 (1970)] urease active soil (Hastings silt loam) was moistened to a moisture content of 20 percent and preincubated at room temperature for 2 days. The preincubated soil (100 g) was then well mixed with 20 ml of water, 410 mg of urea, or 410 mg of urea plus 41 mg of inhibitor and placed in a cylindrical polystyrene container (6×9.8 cm) and incubated at 25° C. for the desired reaction period. The soil from each container was thoroughly mixed and a 100-g sample was extracted with 250 ml of 2M KCl containing 5 ppm of phenyl phosphorodiamidate to prevent urea hydrolysis during handling. The urea in the extracts was determined colorimetrically as a measure of the unhydrolyzed urea. The results of 1-day, 3-day, and 6-day tests are given in Table V below. The results demonstrate that 2-phenoxy-2,4,4,6,6-pentaaminocyclotriphosphazatriene and 2,4-diphenoxy-2,4,6,6-tetraaminocyclotriphosphazatriene have soil urease inhibitory properties comparable to phenyl phosphorodiamidate for the 1-, 3-, and 6-day tests. The soil urease inhibitory properties of 2,4,6-triphenoxy-2,4,6-triaminocyclotriphosphazatriene and 2,2,4,4,6,6-hexaaminocyclotriphosphazatriene are less than that of phenyl phosphorodiamidate in the well-mixed system.

TABLE V

Urea Remaining Unhydrolyzed in Three Replications in Hastings Silt Loam Soil Incubated at 25° C. in the Presence of Compounds Tested for Urease Inhibition in a Well-Mixed System

| N Source | Weight, mg | Inhibitor | Weight, mg | Unhydrolyzed Urea, % Well-Mixed | | |
|---|---|---|---|---|---|---|
| | | | | 1-Day | 3-Day | 6-Day |
| Urea | 410 | $P_3N_3(NH_2)_5(OC_6H_5)$ | 41 | 96 | 82 | 44 |
| Urea | 410 | $P_3N_3(NH_2)_4(OC_6H_5)_2$ | 41 | 94 | 74 | 36 |
| Urea | 410 | $P_3N_3(NH_2)_3(OC_6H_5)_3$ | 41 | 82 | 37 | 0 |
| Urea | 410 | $P_3N_3(NH_2)_6$ | 41 | 86 | 57 | 9 |
| Urea | 410 | $(C_6H_5O)PO(NH_2)_2$ | 41 | 100 | 99 | 46 |
| Urea | 410 | — | — | 80 | 13 | 0 |

EXAMPLE V 2-phenoxy-2,4,4,6,6-pentaaminocyclotriphosphazatriene, 2,4-diphenoxy-2,4,6,6-tetraaminocyclotriphosphazatriene, and 2,4,6-triphenoxy-2,4,6-triaminocyclotriphosphazatriene were prepared as described in Example IV, supra. The relative urease inhibitory characteristics were tested using Hastings silt loam and a banded system as described in Example I, supra. The results of 3-day and 6-day tests are given in Table VI below.

TABLE VI

Urea Remaining Unhydrolyzed in Three Replications in Hastings Silt Loam Soil Incubated at 25° C. in the Presence of Compounds Tested for Urease Inhibition in a Banded System

| N Source | Weight, mg/Band | Inhibitor | Weight, mg/Band | Unhydrolyzed Urea, % Banded | |
|---|---|---|---|---|---|
| | | | | 3-Day | 6-Day |
| Urea | 410 | $P_3N_3(NH_2)_5(OC_6H_5)$ | 41 | 61 | 7 |
| Urea | 410 | $P_3N_3(NH_2)_4(OC_6H_5)_2$ | 41 | 60 | 4 |
| Urea | 410 | $P_3N_3(NH_2)_3(OC_6H_5)_3$ | 41 | 21 | 0 |
| Urea | 410 | $P_3N_3(NH_2)_6$ | 41 | 64 | 8 |
| Urea | 410 | $(C_6H_5O)PO(NH_2)_2$ | 41 | 82 | 24 |
| Urea | 410 | — | — | 21 | 0 |

The results show that 2-phenoxy-2,4,4,6,6-pentaaminocyclotriphosphazatriene, 2,4-diphenoxy-2,4,6,6-tetraaminocyclotriphosphazatriene, and 2,2,4,4,6,6-hexaaminocyclotriphosphazatriene inhibit soil urease during the 3-day and 6-day tests.

EXAMPLE VI 2-phenoxy-2,4,4,6,6-pentaaminocyclotriphosphazatriene, 2,4-diphenoxy-2,4,6,6-tetraaminocyclotriphosphazatriene, 2,4,6-triphenoxy-2,4,6-triaminocyclotriphosphazatriene, 2,2,4,4,6,6-hexaaminocyclotriphosphazatriene were prepared as described in Examples I and IV, phosphoryltriamide and phenyl phosphorodiamidate were used as reference, supra. The soil urease inhibition was tested using Crowley silt loam and a well-mixed system modified from that of Douglass and Bremner [L. A. Douglas and J. M. Bremner, *Soil Biol. Biochem.* 3:309–315 (1971)]. The results of the tests are given in Table VII below.

TABLE VII

Urease Inhibition in Percent in Three Replications in Crowley Silt Loam Soil Incubated at 30° C. in the Presence of Compounds Tested for Urease Inhibition in the Extended Time Evaluation System

| | Soil Urease Inhibition[a] Days | | | | |
|---|---|---|---|---|---|
| | 0 | 3 | 7 | 14 | 21 |
| | | | (%) | | |
| $P_3N_3(NH_2)_5(OC_6H_5)$ | 95 | 75 | 49 | 42 | 44 |
| $P_3N_3(NH_2)_4(OC_6H_5)_2$ | 75 | 94 | 71 | 69 | 65 |
| $P_3N_3(NH_2)_3(OC_6H_5)_3$ | 22 | 79 | 74 | 84 | 82 |
| $P_3N_3(NH_2)_6$ | 46 | 23 | 20 | 4 | 4 |
| $(C_6H_5O)PO(NH_2)_2$ | 100 | 35 | 27 | 4 | 0 |
| $PO(NH_2)_3$ | 29 | 4 | 12 | 0 | 0 |

[a]L. A. Douglass and J. M. Bremner, Soil Biol. Biochem. 3:309–315 (1971).

Specifics of the procedure for evaluating the test compounds in Example VI are as follows. Urease active soil (Crowley silt loam from Louisiana) was moistened to a moisture content of 16% (dry weight basis) and preincubated at room temperature for 2 days. One milliliter of solution or suspension containing 7 micromoles of each test compound was added to 120 g of moist soil and mixed well. Polyvinylchloride cylinders, 12 cm long and 4 cm in diameter, were filled with the inhibitor-soil mixture and packed to a bulk density of about 0.9 g/cm$^3$ and covered with a perforated plastic film. These columns of inhibitor-soil mixtures plus untreated check columns were incubated at 30° C. for periods of 0, 3, 7, 14, and 21 days at constant moisture content. At each time interval, 1 ml of urea solution containing 50 mg of urea was mixed well with the inhibitor-soil mixture from a single column. The urea-inhibitor soil mixture was packed in a column to a bulk density of about 0.9 g/cm$^3$, covered with a perforated plastic film, and reincubated for 16 hours at 30° C. Following the 16 hours of reincubation, about 120 g of the urea-inhibitor-soil mixture was extracted with 250 ml of 2M KCl containing 5 ppm of phenylphosphorodiamidate. The KCl-PPDA extracts were analyzed on the Auto Analyzer II [Technicon method No. 40001 FD4, Technicon, Tarrytown, N.Y., U.S.A. (1974)]. Three replicates were used on all treatments and checks.

This modification of the inhihitor-soil-urea evaluation procedure permits the measurement of urease inhibition in a system that is independent of the time of urea addition. This contrasts with the conventional methods used to collect the data presented in FIG. 1 and Tables II to V. The data in Tables II to V in part show that essentially all urea in the uninhibited soil tests was hydrolyzed by the soil urease in 6 days or less. In the modified procedure, supra, the unhydrolyzed urea in the uninhibited soil samples averaged 66–70% at the time of analysis for time periods up to 21 days, thus verifying the advantage of this procedure in comparison with the conventional methods.

In FIG. 1 the conventional test shows that none of the test compounds are effective inhibitors beyond about 10 days. However, when the same compounds are tested in the time independent modified soil evaluation procedure, the results (FIG. 2) show that three of the four test compounds, all phenoxy derivatives, are clearly superior to the reference standard PPDA during the 21-day test period. The fourth compound—2,2,4,4,6,6-hexaaminocyclotriphosphazatriene—is as good or better than PPDA for the time period from 14 to 21 days.

Figure 2:
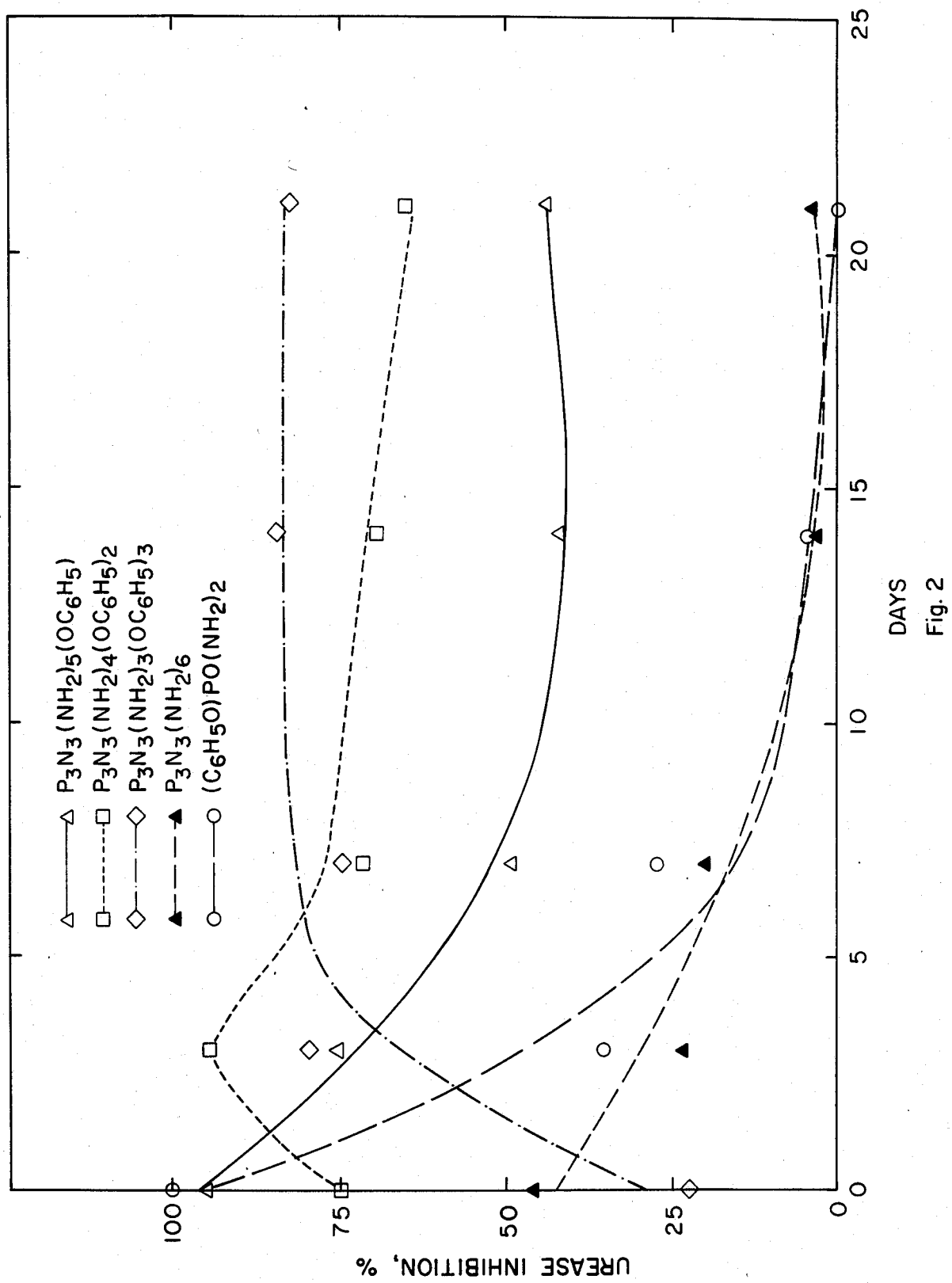
FIG. 2 shows the change in percent urease inhibition for times up to 21 days obtained using a modification of the evaluation procedure that permits measurement of urease inhibition in a system that is independent of time of urea addition as discussed infra, p. 18, lines 14∼.

FIG. 2 clearly shows that PPDA demonstrates complete (100%), instantaneous urease inhibition at 0 days, but then shows a rapid decrease in percent urease inhibition (only 35% inhibition at 3 days and 0% inhibition at 21 days). All of the cyclotriphosphazatrienes have lower initial percent urease inhibition than PPDA as well as individual and characteristic inhibition rates. In the case of the hexaaminocyclotriphosphazatriene, its percent inhibition equals or exceeds that of the reference PPDA for periods longer than 14 days and after 21 days this compound still exhibits some urease inhibition (about 4%) while PPDA shows no inhibition. For time periods greater than 3 days, the phenoxy-substituted cyclotriphosphazatrienes show high percentages of urease inhibition (between 75% and 94%) and were able to sustain urease inhibition at levels between 50% and 84% during the period from 7 to 21 days. During the early time period (0 to 7 days), S[$P_3N_3(NH_2)_5(OC_6H_5)$] and [$P_3N_3(NH_2)_4(OC_6H_5)_2$] maintained high levels of percent urease inhibition, but their effectiveness declined slightly during the period between 7 and 21 days. However, during the period between 7 and 21 days, [$P_3N_3(NH_2)_3(OC_6H_5)_3$] was able to maintain urease inhibition at levels greater than 80%. Thus, it is apparent from FIG. 2 that systematic increases in the degree of phenoxy substitution changes the pattern of inhibition of the cyclotriphosphazatrienes with the result that a high percentage of urease inhibition of soil urease activity can be maintained for periods of at least 21 days.

Thus, only the clear elucidation of the sustained time inhibition of urease activity by the test compounds by the modified evaluation procedure makes it possible to understand that physical mixing of the substituted cyclotriphosphazatriene derivatives in various proportions will provide sustained percentage urease inhibition at preselected levels and for preselected time periods that can be controlled by varying the quantity of specific test compounds in the formulation.

To illustrate the use of mixtures of the test compounds to provide sustained urease inhibition for extended time periods, the data (in part) from Table VII in Example VI have been used to calculate the inhibition of some two- and three-component mixtures. These examples have been selected for convenience and clarity and similar results could have been obtained using other 2-, 3-, and 4-component mixtures to obtain similar levels of percent urease inhibition for extended time periods.

Figure 3:
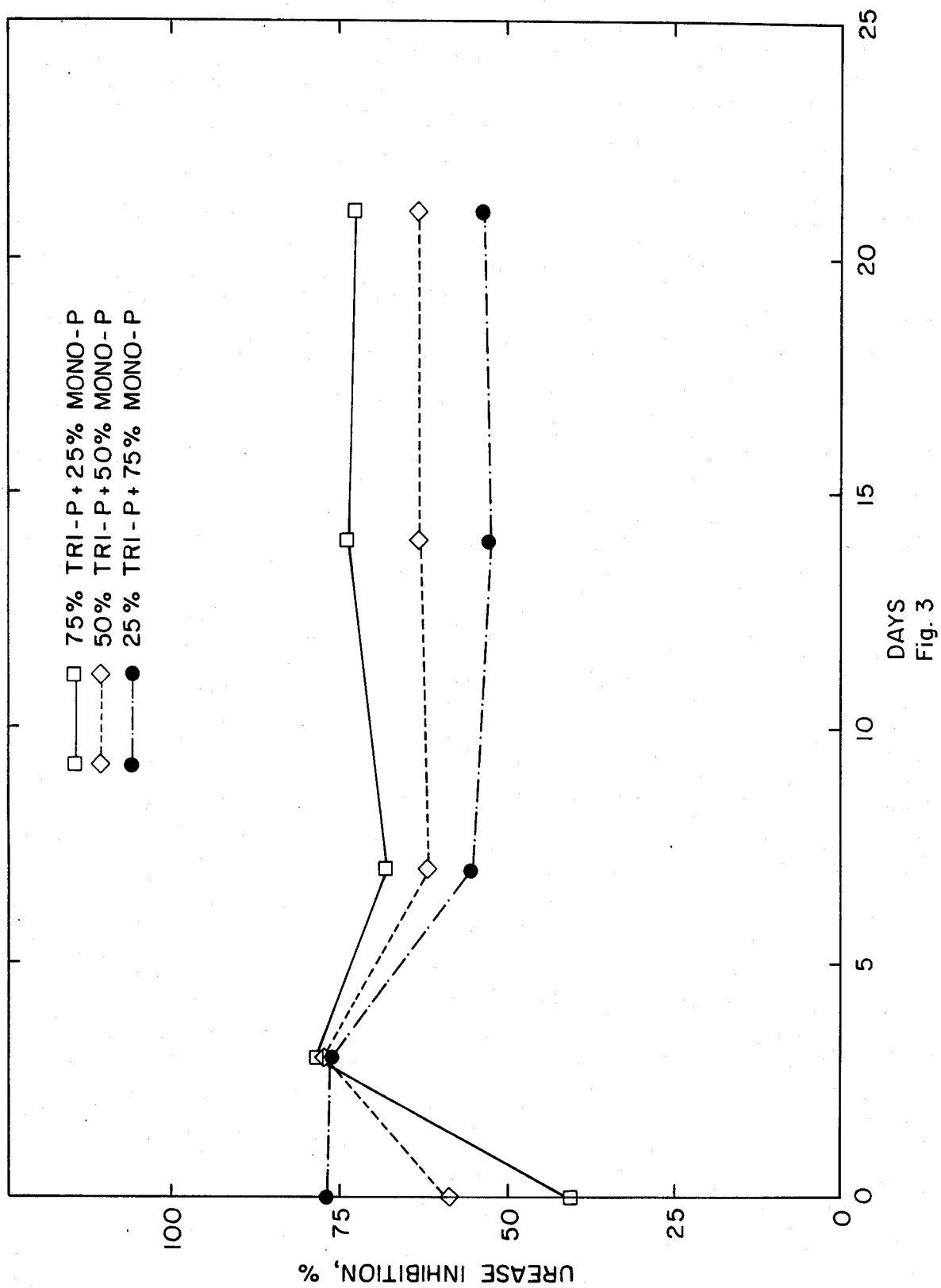
FIG. 3 and FIG. 4 show the calculated percent urease inhibition that can be obtained using physical mixtures of some of the test compounds. For the sake of convenience and a better understanding.

The binary mixtures were calculated using two phenoxy-substituted cyclotriphosphazatrienes [$P_3N_3(NH_2)_5(OC_6H_5)$] and [$P_3N_3(NH_2)_3(OC_6H_5)_3$]. All the mixtures shown in FIG. 3 will provide 50% to 80% urease inhibition for time periods of 3 days and extending up to at least 21 days. Monte Carlo statistical simulations show that a mixture of 50% [$P_3N_3(NH_2)_5(OC_6H_5)$] and [$P_3N_3(NH_2)_3(OC_6H_5)_3$] will provide an essentially linear urease inhibition at 65% urease inhibition for the time period from 0 to 21 days.

Figure 4:
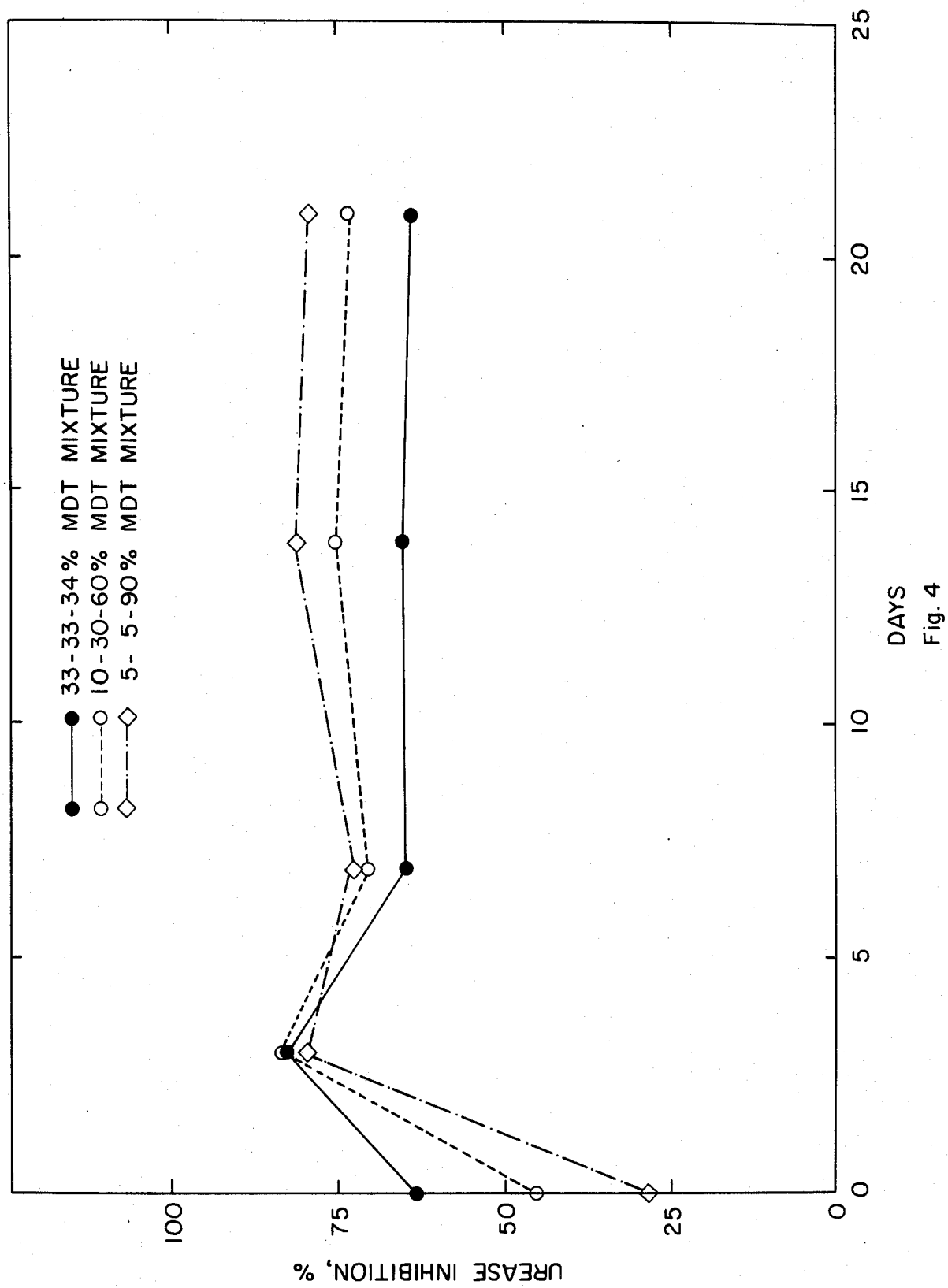

Similarly, the tertiary mixtures shown in FIG. 4 were calculated by adding the third phenoxy-substituted cyclotriphosphazatrienes [$P_3N_3(NH_4)_4(OC_6H_5)_2$] to the phenoxy-substituted cyclotriphosphazatrienes used in the binary mixture calculations. The results shown in FIG. 4 show that tertiary mixtures will provide 60% to 80% urease inhibition for time periods of 3 days and extending to at least 21 days.

The high initial percentage urease inhibition (up to 7 days) results from [$P_3N_3(NH_2)_5(OC_6H_5)$] component of the mixtures while the percentage of urease inhibition between 7 days and 21 days results from the combined effects of [$P_3N_3(NH_2)_4(OC_6H_5)_2$] and [$P_3N_3(NH_2)_3(OC_6H_5)_3$].

Thus, the combination of the various individual inhibition curves and the specific desirable inhibition rates will allow the development of optimal mixtures of substituted cyclotriphosphazatriene derivatives, especially the phenoxy-substituted derivatives, with specified time and inhibition intensity characteristics to meet the demands of a wide variety of agroclimatic, soil, crop, and management conditions and practices.

While we have shown and described particular embodiments of the present invention, modifications and variations thereof will occur to those skilled in the art. We wish it to be understood, therefore, that the appended claims are intended to cover such modifications and variations which are within the true scope and spirit of the present invention.

What we claim as new and desire to secure by Letters Patent of the United States is:

1. A composition of matter eminently suitable for substantially sustaining the control of enzymatic decomposition of urea in soil systems, said enzymatic decomposition of said urea being to ammonia and carbonic acid and being due to the action of the enzyme urease thereupon, said new composition of matter having the formula:

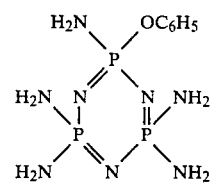

2. A composition of matter eminently suitable for substantially sustaining the control of enzymatic decomposition of urea in soil systems, said enzymatic decomposition of said urea being to ammonia and carbonic acid and being due to the action of the enzyme urease thereupon, said new composition of matter having the formula:

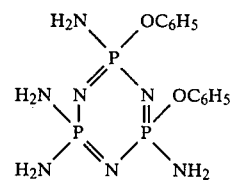

3. A composition of matter eminently suitable for substantially sustaining the control of enzymatic decomposition of urea in soil system, said enzymatic decomposition of said urea being to ammonia and carbonic acid and being due to the action of the enzyme urease thereupon, said new composition being a mixture of matter having the formulae:

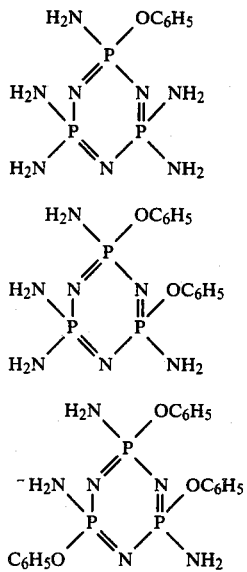

and mixed in such a fashion so as to contain 10 to 90 percent M and either 10 to 90 percent D or 10 or 90 percent T, the exact percentages of M and D or T being dependent and directly proportional to the desired rate and length of control of said enzymatic decomposition.

4. A composition of matter eminently suitable for substantially sustaining the control of enzymatic decomposition of urea in soil systems said enzymatic decomposition of said urea being to ammonia and carbonic acid and being due to the action of the enzyme urease thereupon, said new composition being a mixture of matter having the formulas:

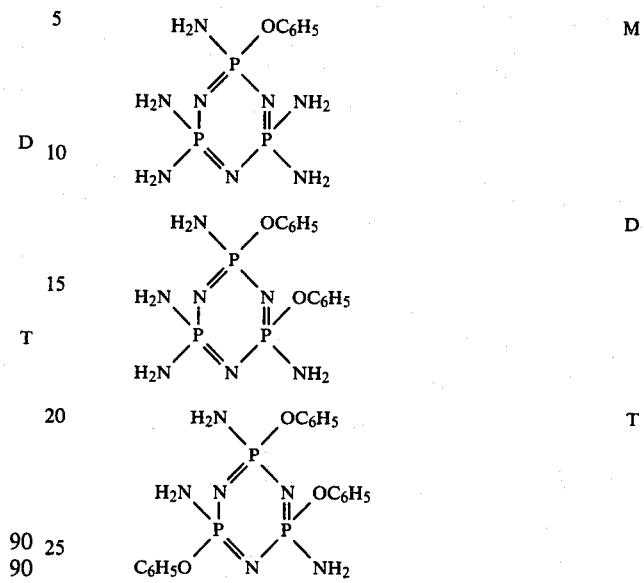

and mixed in such a fashion as to contain 10 to 90 percent M and 10 to 90 percent D and 10 to 90 percent T, the exact percentages of M and D or T being dependent on the desired rate and length of control of enzymatic decomposition.

* * * * *